US007967740B2

(12) United States Patent
Mertens et al.

(10) Patent No.: US 7,967,740 B2
(45) Date of Patent: Jun. 28, 2011

(54) THERAPEUTIC DEVICES FOR THE TREATMENT OF VARIOUS CONDITIONS OF A FEMALE INDIVIDUAL

(75) Inventors: Jane U. Mertens, Del Mar, CA (US); Dean Bauer, Del Mar, CA (US)

(73) Assignee: Ohmea Medical Technologies, Inc., Del Mar, CA (US)

( * ) Notice: Subject to any disclaimer, the term of this patent is extended or adjusted under 35 U.S.C. 154(b) by 816 days.

(21) Appl. No.: 11/847,598

(22) Filed: Aug. 30, 2007

(65) Prior Publication Data

US 2008/0071138 A1 Mar. 20, 2008

Related U.S. Application Data

(60) Provisional application No. 60/824,032, filed on Aug. 30, 2006.

(51) Int. Cl.
*A61F 5/00* (2006.01)

(52) U.S. Cl. .......... 600/38

(58) Field of Classification Search .......... 600/19, 600/20, 38–41; 601/6–11, 112, 113, 80, 601/82, 85; 606/201–203
See application file for complete search history.

(56) References Cited

U.S. PATENT DOCUMENTS

| | | | | | |
|---|---|---|---|---|---|
| 2,234,102 | A | * | 3/1941 | Lloyd | 601/101 |
| 2,314,590 | A | * | 3/1943 | McCarty | 601/8 |
| 2,519,790 | A | * | 8/1950 | Quinn | 601/6 |
| 5,725,473 | A | | 3/1998 | Taylor | |
| 5,797,859 | A | * | 8/1998 | Prehodka | 601/22 |
| 5,925,002 | A | * | 7/1999 | Wollman | 601/70 |
| 6,032,313 | A | * | 3/2000 | Tsang | 15/22.1 |
| 6,464,653 | B1 | * | 10/2002 | Hovland et al. | 601/7 |
| 2003/0073881 | A1 | | 4/2003 | Levy | |

OTHER PUBLICATIONS

International Search Report of the International Searching Authority for International Application No. PCT/US2007/077293, issued Mar. 6, 2008.

* cited by examiner

*Primary Examiner* — Samuel G Gilbert
(74) *Attorney, Agent, or Firm* — Procopio Cory Hargreaves & Savitch LLP; Noel C. Gillespie

(57) ABSTRACT

This invention relates to devices targeted to resolving various conditions of a female patient in need thereof, the conditions being female sexual dysfunction and urinary incontinence. The present disclosure provides for a device which incorporates a variety of elements in an effort to treat certain conditions of a female individual in need thereof. Optionally, the device of the present invention may be used as a prophylactic measure to prevent a condition selected from the group consisting of female sexual dysfunction and urinary incontinence.

32 Claims, 3 Drawing Sheets

THERAPEUTIC DEVICES FOR THE TREATMENT OF VARIOUS CONDITIONS OF A FEMALE INDIVIDUAL

CROSS REFERENCE TO RELATED APPLICATION

This application claims priority to U.S. Provisional Application No. 60/824,032 filed Aug. 30, 2006 and the contents thereof are incorporated herein in their entirety.

TECHNICAL FIELD OF THE INVENTION

This invention relates to devices targeted to resolving various conditions of a female patient in need thereof, the conditions being female sexual dysfunction and urinary incontinence.

BACKGROUND OF THE INVENTION

The Diagnostic and Statistical Manual of Mental Disorders (DSM-IV-TR) identifies female sexual arousal disorders and female orgasmic disorders as specific diagnoses.

Statistical estimates vary greatly, but it is thought that the overall prevalence of female orgasmic disorders may be up to 76% of all women (Berraan et al. *Curr Opin Urol.* 1999 November; 9(6):563-8).

There are several medical conditions—diabetes, thyroid disorders, etc. that can affect orgasmic ability (Bultrini et al., *J Sex Med.* 2004 November; 1(3):337-40; Dorurk et al., *Arch Androl.* 2005 January-February; 51(1):1-6). Additionally, many medications themselves also have this potential, such as blood pressure medicines and anti-depressants (Okeahialam et al., *J Natl Med Assoc.* 2066 April; 98(4):638-40*; Harv Mens Health Watch.* 1999 February; 3(7):7-8; Story, *J Sex Res.* 1974 May; 10(2):132-49).

Researchers have been cognizant of the observations that the above identified conditions and medicaments result in decreased or hindered blood flow to the clitoral region of females, thus causing or, at a minimum, exacerbating such problems (Berman et al., *Curr Opin Urol.* 1999 November; 9(6):563-8; Park et al., *J Urol.* 2002 September; 168(3):1269-72).

The female sexual response cycle is divided into four phases: (1) excitement; (2) plateau; (3) orgasm; and (4) resolution. The device of the present invention is intended to focus specifically on the most difficult transition, namely from plateau to orgasm.

The clitoris is the most sensitive sexual body part. It is the only organ in the human body to have no other function than pleasure. The clitoris is comprised of the glans (head), the shaft (continuing towards the pubic bone), and divides into two "legs" (crura) that surround the vaginal opening with erectile tissue (the vestibular bulbs). Typically, the general reference to the clitoris usually means the glans.

During orgasm, the clitoris becomes erect from blood—engorgement—and pulls under the hood of the clitoris.

Mechanical treatment approaches have included vibrators, and one device uses a suction pump placed on the clitoris to create engorgement with manually controlled pulsation (Billups et al., *J Sex Marital Ther.* 2001 October-December; 27(5):435-41; U.S. Pat. No. 6,464,653). This device applies vacuum pressure to the clitoris in an effort to promote engorgement of the clitoris with blood.

There are several U.S. Patents related to similar devices in an effort to treat the various conditions related herein. U.S. Pat. No. 6,464,653 ('653) describes a device and method for treating female sexual dysfunction that promote blood flow to the genital region, specifically the clitoris of a female patient. The background section discusses the problem of female erectile dysfunction and clitoral blood flow. The '653 patent references Park et al., a study that shows collagen can build up in the clitoral blood vessels when arterial inflow to the clitoris is compromised.

Clitoral erectile insufficiency or reduced clitoral arterial flow may be caused by atherosclerosis, diabetes, or age-related causes, among other factors. Reduced clitoral arterial flow may lead to fibrosis of the clitoral cavernosa and reduced clitoral physiological function. In an animal model, researchers demonstrated that significant collagen synthesis occurs when the arterial inflow to the clitoris is compromised. This work demonstrated the importance of maintaining arterial flow to the clitoris to prevent collagen synthesis and fibrosis on the smooth muscle (Park; et al., *Int J Impot Res.* 9:27-37, 1997).

It is believed that the difficulty or inability to achieve clitoral tumescence may be related to and associated with other symptoms of female sexual arousal disorder. Clitoral stimulation and tumescence are important aspects of female sexual arousal. Tumescence or engorgement occurs when the clitoris fills with blood and, during sexual arousal, the smooth muscles within the clitoris relax and the arterial walls dilate. This results in an increase in blood flow leading to tumescence and extension of the glans clitoris.

According to the International Consensus Report on Female Sexual Dysfunction, Female Sexual Arousal Disorder (FSAD) is defined as the persistent or recurrent inability to attain or maintain adequate genital lubrication or swelling responses resulting in personal distress. FSAD may be expressed as a lack of subjective excitement or lack, of genital (lubrication/swelling) or other somatic responses (AFUD Consensus Report of FSD, 1998).

The device of the '653 patent is designed to increase blood flow in the clitoris to assist a woman to achieve clitoral engorgement, and are applicable to the treatment and diagnosis of female sexual disorders. Such designs are meant to increase blood flow by creating a vacuum around the clitoris.

However, one of the major limitations of the '653 device is the immediate area to which the suction pressure is applied. The suction pressure is only applied directly to the clitoris. The surrounding tissues will fail to be accessed for recruitment of additional capillaries in order to increase arterial flow to the clitoris. Furthermore, even if the '653 device were extended to regions outside of the clitoris proper, the suction pressure alone is unlikely to resolve the negative effects of collagen buildup in the surrounding areas of the clitoral tissues. Collagen synthesis and resulting buildup are best dealt with through a means of physical assault upon the relevant area, namely through external physical pressure against and/or stimulation to the relevant area.

The device of the '653 patent also includes a battery-operated vacuum pump and a disposable vacuum cup, wherein the vacuum cup is placed over the clitoris and the pump is activated to create a vacuum which draws blood into the clitoris, causing tumescence. The vacuum cup is attached to the vacuum pump and is activated by a button or switch on the vacuum pump or a housing thereof. A control valve, e.g. on an opposite side of the vacuum pump or housing, controls the amount of vacuum applied. By manually covering and uncovering the aperture with e.g. a finger of the patient or of the patient's partner, suction pressure in the suction applicator can be varied, rapidly if desired, to promote stimulation of the clitoral region. Additionally, modulation of suction pressure serves to refresh arterial blood flow in the clitoris. By cycling arterial blood through the clitoris, the blood is better able to pick up collagen and accelerate its removal. Removal of collagen build-up and fibrosis on the smooth musical thus is facilitated and encouraged. However, as discussed supra, vacuum pressure alone is unlikely to be the most effective means of accomplishing such a task.

The '653 device must therefore rely on a manually operated vacuum pump in order to cycle through on-and-off stages of the device. This is far from an optimal design in that it is incumbent upon the device user to control the cycling of the vacuum in order to deliver the suction pressure to the clitoris. This is yet another limitation of the prior art device which is remedied by the device of the present invention. Moreover, having vacuum pressure alone is insufficient to increase the arterial flow to the clitoral region for proper clitoral tumescence, irrespective of the size of the vacuum cup through which such pressure is delivered. What is needed is a means of combining such vacuum pressure with additional features, thereby enabling the device to recruit blood flow from additional regions in an effort to achieve tumescence or engorgement.

The device of the '653 patent offers a long-term treatment solution, with results not expected for several weeks of regular use. This provides for a diminished likelihood of device use for those individuals in need of immediate treatment.

There is a current need in the field for the present invention, as there has been no previous device available which combines mechanical vibration, suction and oscillation, in one machine.

SUMMARY OF THE INVENTION

The present disclosure teaches a device which incorporates a variety of elements in an effort to treat certain conditions of a female individual in need thereof. Optionally, the device of the present invention may be used as a prophylactic measure to prevent a condition selected from the group consisting of female sexual dysfunction and urinary incontinence.

One embodiment of the device of the present invention includes suction, oscillation, and vibration elements which will enable the patient to electronically modulate the separate elements, using the control mechanisms, or a combination, described above. The device's vacuum modulation control differs from the '653 device in that it does not feature a hole to be manually covered and uncovered to modulate the pressure. By mechanically modulating the vacuum pressure and rhythm, while applying oscillation and vibration to the clitoris or clitoral region, blood flow to the clitoris is refreshed. By cycling arterial blood through the clitoris with vacuum, oscillation, and vibration therapy, the blood will better be able to pick up collagen and accelerate its removal. Removal of collagen build-up and fibrosis on the smooth muscle thus is facilitated and encouraged.

Another embodiment of the device of the present invention combines direct suction on the clitoral head, stimulates the surrounding clitoral tissue and promotes the directed aggregation of blood flow to the surrounding tissues, thereby optimizing orgasmic potential.

Another embodiment of the device of the present invention may be used in the treatment of urinary incontinence in a female individual in need thereof. The prior art devices above have applied pressure to the sacral nerves in an effort to treat urinary incontinence. The sacral nerves have been shown to impact, in particular, the bladder and the pelvic floor muscles. However, a more direct effect on urinary incontinence would likely be achieved through the recruitment of arterial blood flow from outside of the immediate clitoral region.

It is known that part of the problem associated with female sexual dysfunction stems from diminished arterial flow to the clitoral region, thereby diminishing tumescence and restricting clitoral engorgement. This can result in the inability to achieve orgasm.

One aspect of the present invention involves the aggregation of capillaries and the associated blood flow from outside of the immediate clitoral region to be directed in order to increase clitoral tumescence. There have been reports of the relatedness between female sexual dysfunction and urinary incontinence (Aslan et al., *Int J Impot Res.* 2005 May-June; 17(3):248-51; Vierhout et al., *Eur J Obstet Gynecol Reprod Biol.* 1993 November; 52(1):45-7; Scott et al., *Am J Obstet Gynecol.* 1979 Nov. 1; 135(5):663-5) It is believed that the aggregation of arterial flow into the clitoral region will stimulate sufficient tumescence in order to assist in the treatment of urinary incontinence Researchers in the field have noted that collagen synthesis around the clitoral region has an inhibitory effect on the arterial flow to the clitoris (Kilinc et al., *Asian J Androl.* 2003 March; 5(1):37-41). It is this inhibition that some believe leads directly to the inability to achieve orgasm. One of the devices of the prior art was designed to apply suction pressure directly to the clitoris in hopes of preventing or disrupting collagen synthesis in the regional tissues, thus physically removing the negative impact upon the capillaries, thus allowing clitoral tumescence/engorgement and prompting the transition from plateau to orgasm in a female individual.

Another embodiment of the device of the present invention includes an oscillation element, which will expound upon the suction pressure concept, with control being mechanically rather than manually supplied, to provide a more effective, reliable and even faster means of transitioning from the plateau phase to orgasm phase. The oscillation element will provide a means of recruiting arterial flow from areas beyond those reached by use of suction pressure only, thereby encouraging the relatively rapid engorgement of the clitoris. Further, the constant oscillation of the tissues will result in a more consistent and reliable means of achieving orgasm when compared to the manual operation of the suction pressure from the prior art. Finally, the direction of oscillation will be focused towards the clitoral region. This will lead to the directed aggregation of increased arterial flow to the region of interest, facilitating even more the consistent and expedient transition from plateau to orgasm.

While promotion of direct clitoral engorgement is important, another feature of the present invention delivers an additional aspect to the treatment of the aforementioned conditions. Specifically, the device of the present invention includes suction, vibratory and oscillatory elements. This tri-functionality is one of the vital components of the device of the present invention which is unique among those of the prior art. The oscillatory element provides a means of recruitment of capillaries outside of the clitoris and directs the aggregation of arterial flow into the clitoral region, thereby increasing the effectiveness of the device. When the oscillatory element is utilized in conjunction with the vibration and suction elements, the present invention provides a reliable means of treating a variety of female disorders, including, but not limited to, female sexual dysfunction and urinary incontinence. Additionally, the entire clitoral area, as opposed to solely the glans, is stimulated.

DESCRIPTION OF THE DRAWINGS

Embodiments of the present invention will be described with respect to the figures, in which like reference numerals denote like elements and in which.

DETAILED DESCRIPTION OF THE INVENTION

Figure 1:
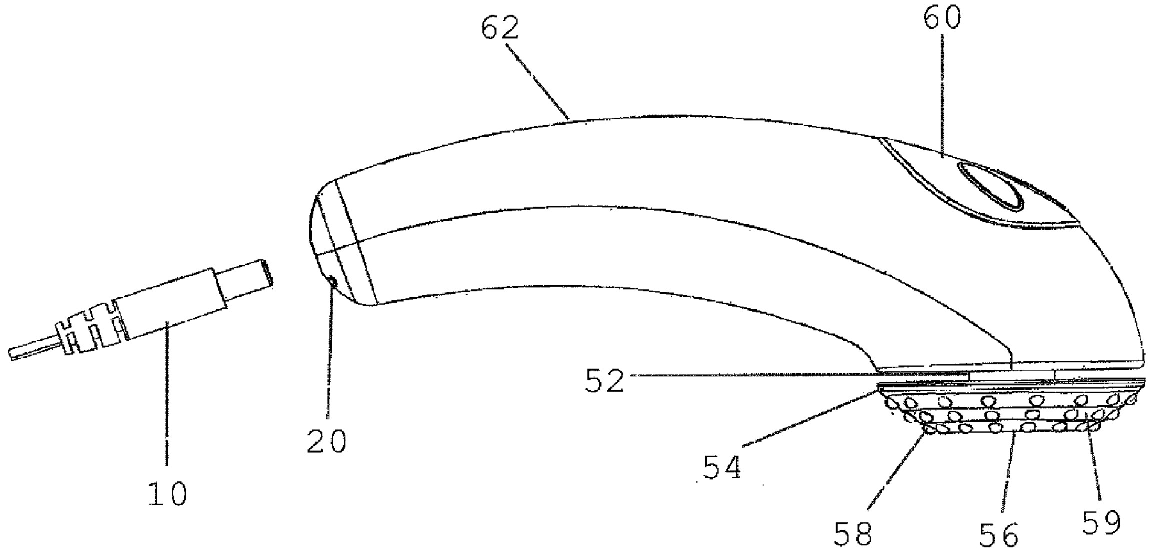
FIG. 1 is a side view of one embodiment of the device of the present invention. It is known that the device will vary slightly from the depiction in FIG. 1 as represented by the varying embodiments disclosed in the present application. For instance, the oscillatory disc 54 is depicted as being at the device end. Optionally, the oscillatory disc 54 may be moved towards the center of the device.
Figure 2:
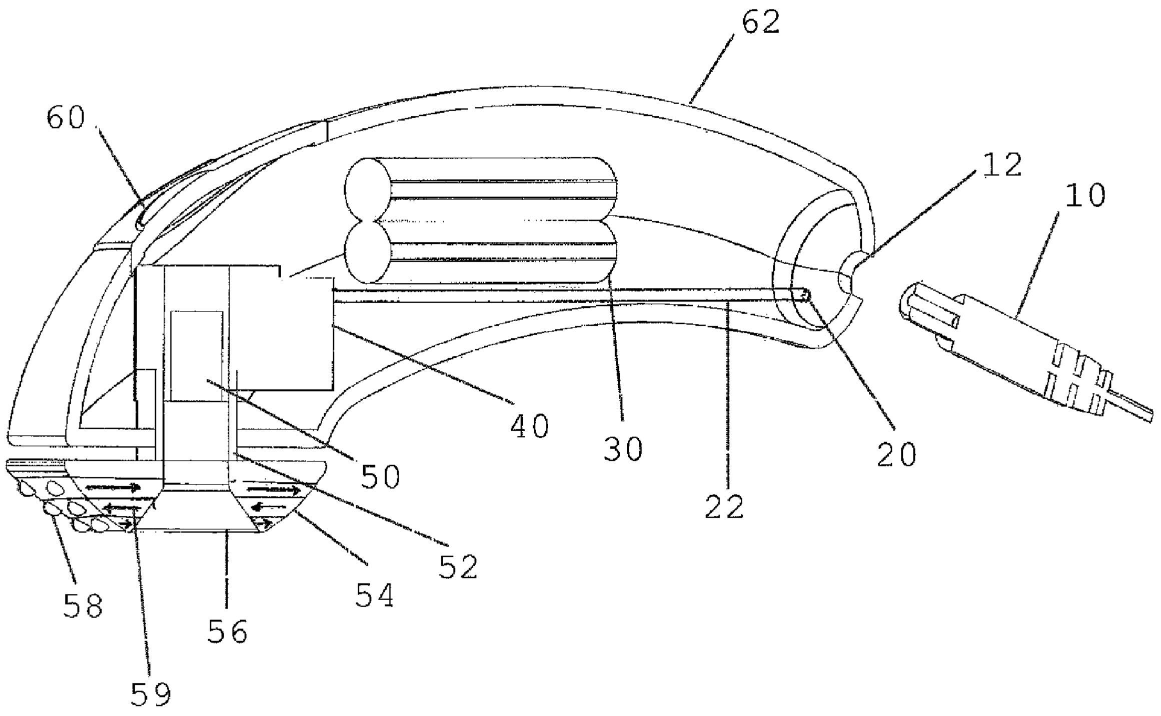
FIG. 2 depicts one embodiment of the device of the present invention. This depiction is a cross-sectional view along the longitudinal axis. The oscillatory disc is viewed from the perspective of multiple nodes at the surface of the disc, which come into contact with the clitoral region. There is also a depiction of the node direction at each of the tracks along the three levels of the oscillatory disc. This cross-sectional view only displays two batteries, even though four batteries are preferably contained in the device.
Figure 3A:
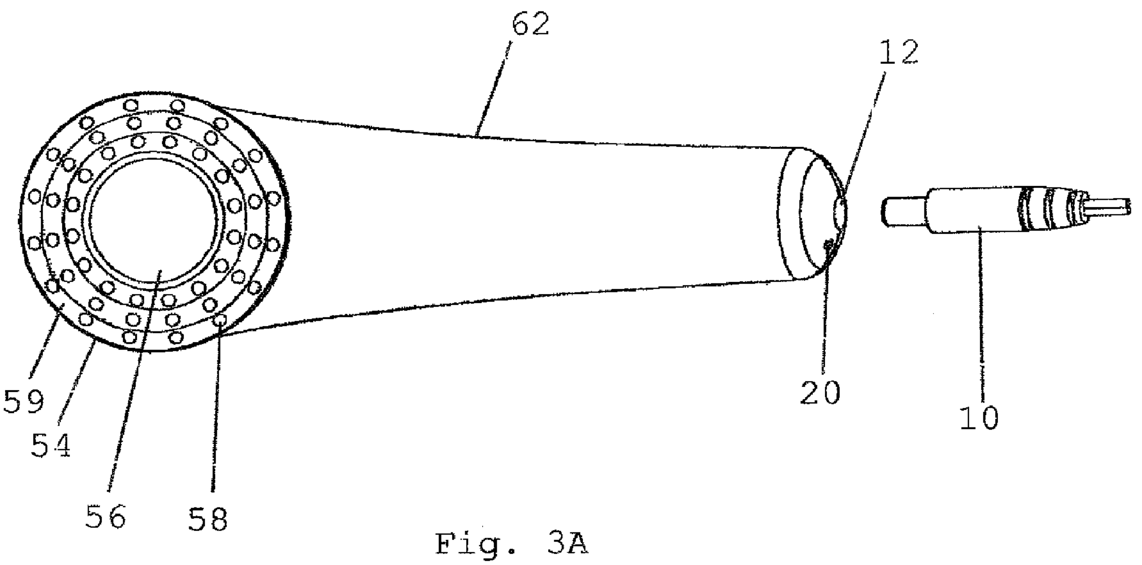
FIGS. 3A and B show a bottom-up view and a top-down view of one embodiment of the device of the present invention, respectively.
Figure 3B:
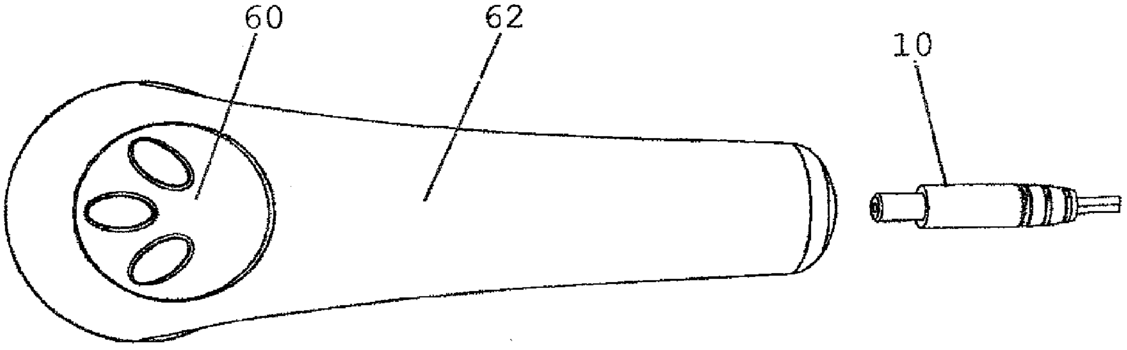

One aspect of the present invention provides a multifunctional device comprising a suction element, vibratory element and an oscillatory element, the elements being powered by a motor delivering a particular degree of force to the elements, with modulation of the force being controlled from the device exterior to operate the elements in order to stimulate clitoral region blood flow in a female individual in need thereof.

Another aspect of the present invention provides for a method of treating female sexual dysfunction, the method comprising a multifunctional device with an interior and exterior comprising a suction element, vibratory element and an oscillatory element, the elements being powered by a motor delivering a particular degree of force to the elements, with modulation of the force being controlled from the device exterior to operate the elements in order to stimulate clitoral region blood flow in a female individual in need thereof.

Another aspect of the present invention provides for a means of delivering urinary incontinence therapy, comprising a multifunctional device with an interior and exterior comprising a suction element, vibratory element and an oscillatory element, the elements being powered by a motor delivering a particular degree of force to the elements, with modulation of the force being controlled from the device exterior to operate the elements in order to stimulate clitoral region blood flow in a female individual in need thereof.

One embodiment of the device of the present invention will increase blood flow in the clitoris by applying suction, oscillation, and vibration to and around the clitoris. The device will provide oscillator therapy, previously unknown in the prior art. Oscillation, in combination with clitoral suction and vibration, will encourage increased blood flow to the clitoris by massaging the clitoris, encouraging clitoral engorgement, and physically breaking down collagen and fibrosis accumulation in the clitoral blood vessels. Increased blood flow will assist the break down of collagen build up in the clitoral arteries. An aspect of the present invention will enable the physical breakdown of collagen through the oscillation element.

Another embodiment of the present invention includes the joint operation of the elements in order to maximize the therapeutic efficacy. Optionally, the elements may be operated individually when desired.

The suction element of the present invention provides an initial means of applying direct pressure to the immediate clitoral region. This is accomplished by placing the compression sheath 56 over the clitoris. The compression sheath 56 is attached to the motor 40 by way of an integrator arm 50. The motor 40 delivers the necessary pressure to the compression sheath 56 in order to invoke initial clitoral tumescence. Optionally, the vibration element can be delivered through the compression sheath 56 when applied to the clitoris.

One aspect of the present invention will be the application of suction to the clitoris through a thin compression sheath 56 that conforms to the patient's clitoris using vacuum force. The vacuum force will be driven by motor 40. One embodiment of the present invention includes a device interface 60, such as a wheel or track which will control the amount of vacuum applied. Most preferably, the device interface 60 will provide for buttons or nodes which will control the multiple elements of the device. The compression sheath 56 is preferably flush with the device housing 62 to create a smooth aesthetic profile. When activated, the compression sheath 56 will extend inward, using vacuum to pull the clitoris flush with or inside the device in order to enact a customized fit in confirmation with the physical dimensions of the patient. The suction force will be modulated by a port tubing 22 which extends out of the device housing 62 through the rear tubing port 20. This will allow the air from the suction to be expunged in order to maximize the pressure applied to the suction element. The suction force, along with the vibration and oscillation forces, applied to the clitoral region will increase blood flow to the clitoris, causing tumescence.

In one embodiment, the compression sheath 56 is preferably constructed from high-grade elastic material, such as a poly vinyl-based material. More preferably, the high-grade elastic material is constructed from a silica-based material. The compression sheath 56 may be embodied as a circular, square, rounded or any other geometric design which may exhibit a conforming structure to the area of the clitoris of a female individual.

In one embodiment, the vibratory element of the present invention provides a means of stimulating the clitoral region via physical motion in order to further enhance clitoral tumescence. The vibratory energy is translated to the oscillatory disc 54 via the motor 40.

The vibratory element will be located in a shape and size such that vibratory force is applied to the clitoral and/or genital region in order to increase blood flow to the clitoris, causing tumescence. The device interface 60 will control the frequency of the vibratory element. The device interface 60 can be located in or, most preferably, on the device housing 62, economically placed for ease of use by the patient.

The oscillatory element of the present invention provides a means of recruiting blood vessels from regions outside of the clitoris in order to promote the aggregation of additional arterial flow directed to the clitoral region. Such an aggregation will facilitate the clitoral tumescence needed for the treatment of female sexual dysfunction and urinary incontinence.

The oscillatory disc 54 will be located at the point of contact with the patient. Most preferably, the oscillatory disc 54 will be located on the underside of device housing 62. Inside of the oscillatory disc 54 will be the preferred location of the oscillatory beads 58. Optionally, the location of the oscillatory beads 58 can be on the outside of the oscillatory disc 54. Preferably, the oscillatory beads travel along the bead tracks 59 in alternating directions. Optionally, the oscillatory beads 58 travel along the bead tracks in the same direction. The bead tracks 59 are positioned around the circumference of the oscillatory disc 54.

One embodiment of the device of the present invention includes one bead track 59 with at least one oscillatory bead 58 progressing around the perimeter of the oscillatory disc 54. More preferably, there can be a plurality of bead tracks 59 with at least two oscillatory beads 58 on each bead track 59.

The overall angle of the oscillatory disc 54 will be positioned such that the oscillation will aggregate blood flow from the genital areas distal to the clitoral region and direct the flow towards the clitoris proper. The oscillatory beads 58 will move along at least one bead track 59, preferably in conjunction with the compression sheath 56 to apply oscillation therapy to the clitoris, increasing blood flow to the clitoris, and causing tumescence. A device interface 60 will control the speed of the oscillatory beads 58. The bead tracks 59 will be located such that when the vacuum element is activated, and the clitoris is pulled flush with, or preferably inside of the device, the oscillatory beads 58 will aggregate arterial blood flow to be directed towards the clitoris in order to achieve tumescence. This feature will enable individualized oscillation therapy according to the unique anatomical features of the patient. The device interface 60 can be located in, or most preferably on, the device housing 62, economically placed for ease of use by the patient.

According to one embodiment, the device is a prescription-only device intended for single patient use. Embodiments of the invention have the potential to be used both as a non-pharmacologic treatment alternative and as a long-term therapy to recondition clitoral smooth muscle and restore normal blood flow and clitoral engorgement by applying suction, oscillation, and vibration forces to the clitoral or general genital region.

Another embodiment of the device of the present invention will include a device housing 62, which accommodates separate control mechanisms operated via a device interface 60 to modulate the intensity of the vacuum, oscillation, and vibration elements. The device will not have flexible tubing, fluid connector, or pliable vacuum cup, extending out from the device, as all vacuum therapy will be generated behind a compression sheath 56. Embodiments of the device may accommodate the vacuum and oscillation elements being readily releasable from the main device, mainly for cleaning purposes. Other embodiments of the device may include waterproofing so the entire device may be cleaned easily with soap and water. Optionally, the compression sheath 56 may be replaced. A further aspect of the present invention includes the oscillatory disc 54 being removed via a quick-release mechanism 52.

According to another embodiment, the device of the present invention will be electrically operated. One embodiment of the present invention includes utilizing at least one lithium rechargeable battery 30. More preferably, the device of the present invention includes use of more than one lithium rechargeable battery 30. Most preferably, the device of the present invention includes a two-by-two configuration of four lithium rechargeable batteries 30. In this embodiment, the batteries 30 could be removed from the device and recharged separately from the device, increasing possibility of discreet device storage and recharging. In an alternative embodiment, the device could use regular non-rechargeable alkaline batteries that would be disposed of and replaced as necessary. In another embodiment, the device of the present invention could be recharged using an A/C adapter 10, with the A/C connection being at the opposite, posterior end of the device at A/C port 12. Optionally, the device of the present invention may be completely powered through the A/C adapter 10.

Another embodiment of the present invention includes a device housing 62, engineered to conform to the curvature of most adult females. The device housing 62 will be fitted and curved to enable comfortable and convenient gripping by a human hand. The device housing 62 and body contact portions can be constructed from biocompatible materials, to ensure that it will not cause adverse tissue reactions when placed in contact with the patient's skin including, but not limited to polymer-based materials such as silicone, polyurethane, polycarbonates, polyester, polyethylene, hydrogels and biodegradable polymers.

Another aspect of the present invention includes the device being waterproof or water resistant to enable cleaning/washing of entire device with an appropriate cleansing solution or soap and water. Another embodiment can accommodate releasing or removing the vacuum and oscillatory elements, preferably in one piece, for easy cleaning with an appropriate cleansing solution or soap and water. The device housing 62 surface texture will preferably be smooth. Optionally, rubberized or silicone grip pads may be applied on each side of the device housing 62 to ensure patient has a firm grip on the device with at least a thumb on one side and some or all other fingers on the other side. The device housing 62 will also be sufficiently sized to accommodate a variety of internal components.

In another embodiment, the device of the present invention enables the vibration force extending into the compression sheath 56 area to vibrate against the clitoris, working in concert with the suction and oscillation therapies via the compression sheath 56 and oscillatory beads 58, respectively. In another embodiment, the vibration therapy could be administered generally, powerful enough to vibrate at or around the clitoris as well as around the general genital region. In another embodiment, the vibration settings could include only localized clitoral vibration or general vibration of the entire patient contact region.

Another aspect of the present invention relates to devices and methods for treating urinary incontinence. Particular embodiments of the invention use a device with variable vacuum, oscillation, and vibration forces to be applied to the female genital region. Embodiments of the invention would apply vacuum and oscillation forces to the clitoral region and/or the vaginal region. Embodiments of the invention would apply vibration force to the region of the female urethral opening, the clitoral or vaginal region, or the general female genital area.

The device of the present invention, according to aspects of the invention, will use a combination of vacuum, oscillation, and vibration to increase blood flow to the female genital region, encouraging contraction of the urethral muscle to alleviate female urinary incontinence. Embodiments of the invention will use clitoral and orgasm stimulation to increase genital blood flow and increase the patient's ability to attain and maintain Kegel muscle contractions. Embodiments of the invention also tend to promote blood flow to the female genital region in an effort to treat female sexual dysfunction if needed.

Embodiments of the invention may result in causing certain nerve responses or otherwise minimizing urinary and/or fecal incontinence in one or more of the various forms, increase blood flow in the clitoris to assist a woman to achieve clitoral engorgement, and otherwise be applicable to the treatment of incontinence and/or the treatment and diagnosis of female sexual disorders. The device of the present invention includes a method of treatment for incontinence which will operate by engorging the clitoris using vacuum, oscillation, and vibration. The oscillation and vibration elements may massage the clitoris to achieve the appropriate muscle relaxation and contraction. Additionally, the oscillation will enable the aggregation of distal arterial blood flow to be directed to the clitoris, greatly enhancing the likelihood of achieving rapid tumescence.

Another aspect of the present invention includes a motor 40 which will achieve its various functions through a series of belts, pulleys or gears. Preferably, the functions of the motor 40 will be carried out by a series of belts, pulleys and gears, which will operate in coordination with engaging and disengaging functionalities relative to the suction, vibration and oscillation elements of the device. Optionally, the motor 40 will be electronically controlled through a microprocessor and circuitry. The motor 40 is preferably located on the central axis with the device housing 62. Each gear from the motor 40 will be attached via a belt mechanism to translate the kinetic energy into the vibration and oscillation elements of the device. Preferably, there is a 1:1 ration of motion to power.

The motor 40 will be preferably centrally located within the device housing 62. Optionally, the motor 40 will be placed towards the front of the device housing 62, based on the ergonomic design of the device of the present invention. The motor 40 will preferably consist of lateral sides. These lateral sides will comprise a smaller axis attached to motor 40 by gears or belts. More preferably, a lever will attach to the main motor 40 in order to drive the elements of vibration and oscillation. Optionally, the lever will attach to motor 40 and, when positioned at one extreme end, will engage all three elements. Additionally, the lever attaches to motor 40 and has an individualized position relative to each of the individual elements (ie. one position for suction, one for vibration and one for oscillation).

We claim:

1. A multifunctional device with an interior and exterior comprising a suction element, a vibratory element and an oscillatory element, the elements being powered by a motor within the device interior delivering a particular degree of force to the elements, with modulation of the force being controlled from the device exterior to operate the elements, wherein each of the suction element, the vibratory element and the oscillatory element is adapted to be applied the clitoral region in order to stimulate clitoral region blood flow in a female individual in need thereof.

2. The device of claim 1, wherein the elements are housed in a housing unit.

3. The device of claim 1, wherein the modulation of the elements by the device operator is accomplished by an interface located on the device exterior.

4. The device of claim 1, wherein the elements may be operated individually.

5. The device of claim 1, wherein the motor applies a force through the suction element, the force modulated via an interface.

6. The device of claim 1, wherein the motor applies a force through the vibratory element, the force modulated via an interface.

7. The device of claim 1, wherein the motor applies a force through the oscillatory element, the force modulated via an interface.

8. The device of claim 1, wherein the oscillatory element is a disc comprising inlaid tracks and beads are rotatably disposed within the tracks.

9. A method of treating female sexual dysfunction, the method comprising a multifunctional device with an interior and exterior comprising a suction element, vibratory element and an oscillatory element, the elements being powered by a motor delivering a particular degree of force to the elements, with modulation of the force being controlled from the device exterior to operate the elements, wherein each of the suction element, the vibratory element and the oscillatory element is adapted to be applied the clitoral region in order to stimulate clitoral region blood flow in a female individual in need thereof.

10. The method of claim 9, wherein the elements are housed in a housing unit.

11. The method of claim 9, wherein the modulation of the elements by the device operator is accomplished by an interface located on the device exterior.

12. The method of claim 9, wherein the elements may be operated individually.

13. The method of claim 9, wherein the motor applies a force through the suction element, the force modulated via an interface.

14. The method of claim 9, wherein the motor applies a force through the vibratory element, the force modulated via an interface.

15. The method of claim 9, wherein the motor applies a force, the force modulated via an interface.

16. The method of claim 9, wherein the oscillatory element is a disc comprising inlaid tracks and beads are rotatably disposed within the tracks.

17. A means of delivering urinary incontinence therapy, comprising a multifunctional device with an interior and exterior comprising a suction element, vibratory element and an oscillatory element, the elements being powered by a motor delivering a particular degree of force to the elements, with modulation of the force being controlled from the device exterior to operate the elements, wherein each of the suction element, the vibratory element and the oscillatory element is adapted to be applied the clitoral region in order to stimulate clitoral region blood flow in a female individual in need thereof.

18. The device of claim 17, wherein the elements are housed in a housing unit.

19. The device of claim 17, wherein the modulation of the elements by the device operator is accomplished by an interface located on the device exterior.

20. The device of claim 17, wherein the elements may be operated individually.

21. The of claim 17, wherein the motor applies a force through the suction element, the force modulated via an interface.

22. The of claim 17, through which the motor applies a force, the force modulated via an interface.

23. The oscillatory element of claim 17, through which the motor applies a force, the force modulated via an interface.

24. The oscillatory element of claim 17, wherein the oscillatory element is a disc comprising inlaid tracks and beads are rotatably disposed within the tracks.

25. A device for stimulation of clitoral blood flow in a female individual in need thereof, the device comprising:

- a housing having dimensions adapted to be held in a user's hand, the housing having a distal end and a proximal end;
- a combination of elements disposed at the distal end of the housing and adapted to be applied to the clitoral region, the combination of elements comprising:
- a suction element comprising a compression sheath formed from a conformable material, wherein a vacuum applied to the compression sheath causes the compression sheath to be drawn inward;
- an oscillatory element comprising at least one disc disposed concentrically around the compression sheath, the disc having a bead track formed therein for rotatably retaining at least one bead;

a motor disposed within the housing and connected to the combination of elements for applying force to produce the vacuum for the suction element and drive the rotation of the at least one bead within the bead track;

a power supply for providing power for operating the motor; and a device interface disposed on the housing for controlling application of power to the motor.

26. The device of claim 25, wherein activation of the suction element moves the at least one bead within the bead track to apply an oscillatory force to tissues surrounding the clitoris.

27. The device of claim 25, wherein the combination of elements further comprises a vibratory element, wherein the motor applies a vibrational force to the at least one disc.

28. The device of claim 25, wherein the oscillatory element includes a plurality of concentric discs and each disc has a plurality of beads rotatably disposed within its bead track, wherein the beads within adjacent discs travel in alternating directions.

29. The device of claim 25, wherein the device interface controls a rotational speed of the at least one bead.

30. The device of claim 25, wherein the device interface includes a separate control for each element of the combination of elements.

31. The device of claim 25, wherein the power supply comprises one or more batteries disposed within the housing.

32. The device of claim 31, wherein the one or more batteries are rechargeable and an A/C adapter is disposed at a proximal end of the housing in electrical communication with the one or more batteries.

* * * * *